(12) United States Patent
Buckler et al.

(10) Patent No.: US 11,593,926 B2
(45) Date of Patent: Feb. 28, 2023

(54) SYSTEMS AND METHODS FOR IMPROVING SOFT TISSUE CONTRAST, MULTISCALE MODELING AND SPECTRAL CT

(71) Applicant: ELUCID BIOIMAGING INC., Boston, MA (US)

(72) Inventors: Andrew J. Buckler, Boston, MA (US); Changguo Ji, Lexington, MA (US); Murali Ayyapillai, Acton, MA (US)

(73) Assignee: ELUCID BIOIMAGING INC., Boston, MA (US)

( * ) Notice: Subject to any disclaimer, the term of this patent is extended or adjusted under 35 U.S.C. 154(b) by 66 days.

(21) Appl. No.: 17/566,439

(22) Filed: Dec. 30, 2021

(65) Prior Publication Data
US 2022/0253992 A1 Aug. 11, 2022

Related U.S. Application Data

(60) Provisional application No. 63/147,609, filed on Feb. 9, 2021.

(51) Int. Cl.
*G06T 5/50* (2006.01)
*A61B 6/00* (2006.01)
(Continued)

(52) U.S. Cl.
CPC .............. *G06T 5/50* (2013.01); *A61B 6/4241* (2013.01); *A61B 6/463* (2013.01); *A61B 6/482* (2013.01); *A61B 6/504* (2013.01); *A61B 6/5247* (2013.01); *G06T 7/0012* (2013.01); *G06T 7/174* (2017.01); *G06T 2207/10081* (2013.01); *G06T 2207/10088* (2013.01); *G06T 2207/10132* (2013.01); *G06T 2207/20216* (2013.01); *G06T 2207/20224* (2013.01)

(58) Field of Classification Search
CPC ......... G06T 5/50; G06T 7/0012; G06T 7/174; G06T 2207/10081; G06T 2207/10088; G06T 2207/10132; G06T 2207/20216; G06T 2207/20224; A61B 6/4241; A61B 6/463; A61B 6/482; A61B 6/504; A61B 6/5247
See application file for complete search history.

(56) References Cited

U.S. PATENT DOCUMENTS

| | | | | |
|---|---|---|---|---|
| 7,599,465 | B2 * | 10/2009 | Walter | A61B 6/4042 378/4 |
| 2003/0215119 | A1 * | 11/2003 | Uppaluri | G06T 7/0012 382/128 |

(Continued)

OTHER PUBLICATIONS

International Search Repot for PCT Appl. No. PCT/US22/11689 dated Apr. 8, 2022.

*Primary Examiner* — Molly Wilburn
(74) *Attorney, Agent, or Firm* — Pearl Cohen Zedek Latzer Baratz LLP

(57) ABSTRACT

Systems and methods for improving soft tissue contrast, characterizing tissue, classifying phenotype, stratifying risk, and performing multi-scale modeling aided by multiple energy or contrast excitation and evaluation are provided. The systems and methods can include single and multi-phase acquisitions and broad and local spectrum imaging to assess atherosclerotic plaque tissues in the vessel wall and perivascular space.

20 Claims, 11 Drawing Sheets

(51) Int. Cl.
  *G06T 7/00*    (2017.01)
  *G06T 7/174*   (2017.01)

(56) References Cited

U.S. PATENT DOCUMENTS

| | | | |
|---|---|---|---|
| 2004/0066881 A1* | 4/2004 | Reddy | A61B 6/507 |
| | | | 600/425 |
| 2006/0067473 A1* | 3/2006 | Eberhard | A61B 6/482 |
| | | | 378/98.9 |
| 2007/0147574 A1* | 6/2007 | Bernard De Man | ......... |
| | | | A61B 6/4241 |
| | | | 378/4 |
| 2007/0189443 A1* | 8/2007 | Walter | G06T 7/136 |
| | | | 378/4 |
| 2008/0198963 A1* | 8/2008 | Spahn | A61B 6/4233 |
| | | | 378/5 |
| 2010/0030069 A1 | 2/2010 | Peter | |
| 2014/0296696 A1* | 10/2014 | Remmele | A61B 8/0875 |
| | | | 600/410 |
| 2016/0262709 A1* | 9/2016 | Siewerdsen | A61B 6/4035 |
| 2017/0265832 A1* | 9/2017 | Antoniades | G16H 50/30 |
| 2017/0360578 A1* | 12/2017 | Shin | G09B 23/286 |
| 2019/0154783 A1* | 5/2019 | Kaditz | G01R 33/5608 |
| 2020/0242761 A1 | 7/2020 | Butler et al. | |
| 2020/0326439 A1 | 10/2020 | Mccollough et al. | |
| 2021/0361972 A1* | 11/2021 | Yi | A61N 5/1043 |

* cited by examiner

SYSTEMS AND METHODS FOR IMPROVING SOFT TISSUE CONTRAST, MULTISCALE MODELING AND SPECTRAL CT

CROSS REFERENCE TO RELATED APPLICATIONS

This application claims the benefit of and priority to U.S. provisional patent application No. 63/147,609, filed on Feb. 9, 2021, the entire contents of which are incorporated herein by reference in its entirety and owned by the assignee of the instant application.

FIELD OF THE INVENTION

The invention relates to computer-aided phenotyping (CAP) of disease which can include applying computerized image analysis and/or data fusion algorithms to patient data. In particular, the invention relates to quantitative imaging and analytics for elucidating the disease process of atherosclerosis, including techniques for improving soft tissue contrast, multi-scale modeling and/or spectral CT.

BACKGROUND OF THE INVENTION

Atherosclerosis can be life threatening, particularly in aging populations, but even among the relatively young. Current methods for diagnosing atherosclerosis, for example, the use of blood markers e.g., cholesterol levels) and/or determining the degree to which the lumen is narrowed (stenosis) are limited, and thus can result in suboptimal treatment decisions (e.g., to perform or not to perform surgeries, or prescribe intensive medical therapy). For example, many vascular surgeries do not benefit the patient, some that need surgeries don't get them, and many could be effectively treated with drugs but may not be prescribed them.

Current tools can analyze a blood vessel lumen, but this can be insufficient for truly diagnosing atherosclerosis, as atherosclerosis is a disease of the vessel wall, rather than the blood or the channel through which it flows. High rates of misclassified risk level, inability to assess likely response to drug therapy, and/or inability to measure response to drugs can occur.

Currently, radiological imagining can be used as a non-invasive and safe method for locating disease origin. Current medical imagining tools can include computed tomography (CT, including single energy, multi-energy, or spectral CT), magnetic resonance imaging (MR, MRA, DCE-MRI, or multi-contrast MRI), ultrasound (b-mode or intravascular US), and targeted contrast agent approaches with various imaging modalities.

Enhanced imaging techniques have made medical imaging an essential component of patient care. Imaging can be valuable because it can provide spatially and temporally localized anatomic and/or functional information, using non- or minimally invasive methods. However, techniques to deal with increasing resolution can be desired, both to exploit patterns and/or signatures in the data typically not readily assessed with the human eye, as well as to, for example, manage a large magnitude of data to efficiently integrate it into the clinical workflow. With newer high-resolution imaging techniques, unaided, the radiologist can "drown" in data. Therefore, in order to, for example, integrate quantitative imaging for individual patient management it can be desirable to provide a class of decision support informatics tools to enable further exploiting the capabilities of imaging within the realities of existing tool work flows and/or reimbursement constraints.

Currently, imaging of atherosclerosis is routinely performed both invasively through catheterization as well as non-invasively by ultrasound, CT, MR, and using nuclear medicine techniques. The most typical assessment is luminal stenosis. Recent progress that has been made has been in the determination of fractional flow reserve.

One difficulty with current imaging of atherosclerosis can include lack of robustness in the method used. For example, current methods typically only provide a low level of contrast between blood vessel outer wall and perivascular tissues, thus making it difficult to distinguish between the two. Some current methods simply employ annular rings around a lumen without specific determination of outer wall boundary. Vessel tapering, branching vessels, nearby tissues, etc. can also be problematic.

Another difficulty with current imaging of atherosclerosis can be due to a particular imaging device interrogating tissue using a limited excitation, and that despite the utility of multi-contrast MR on the one hand, or multi-energy CT on the other, the result can be a degree of non-specific response in the produced signal.

SUMMARY OF THE INVENTION

Advantages of the invention can include improved soft tissue contrast. Some advantages of the invention can include improved characterizing tissue. Some advantages of the invention can include classifying phenotype. Some advantages of the invention can include stratifying risk. Some advantages of the invention can include performing multi-scale modeling aided by multiple energy or contrast excitation and evaluation.

Some advantages of the invention can include application of single vs. multi-phase acquisitions as well as broad spectrum spectral CT to assess atherosclerotic plaque tissues in the vessel wall and perivascular space. Some advantage of the invention can include distributed tissue types, as overlays on focally organized tissues.

In one aspect, the invention involves a computerized method for improving soft tissue analysis. The method can also involve obtaining a plurality of radiological images of patient, where each of the radiological images is obtained using different excitations. The method can also involve selecting a process among a plurality of processes to analyze the plurality of excitations based on an expected soft tissue type. The method can also involve segmenting the processed plurality of excitations to display the soft tissue.

In some embodiments, the plurality of radiological image are computerized tomography (CT) images and the different excitations are different x-ray energy. In some embodiments, the plurality of radiological image are Magnetic Resonance (MR) images and the different excitations are different radio frequency pulses.

In some embodiments, the plurality of radiological image are ultrasound images and the different excitations are different frequencies.

In some embodiments, the invention involves determining, via, the computing device, a first tissue type in a region of interest based on the plurality of radiological images of the patient, wherein the first tissue type is a represented by a grid of points across the region of interest, and determining, via the computing device, a second tissue type, in the region interest based on the plurality of radiological images of the patient, wherein the second tissue type is a focal region in the region of interest, wherein at least some of the grid points of the first tissue type coincide in position with the second tissue type.

In some embodiments, the plurality of processes comprises a digital subtraction process, digital addition process, a multivariate statistical process, or an excitation selection process. In some embodiments, the digital subtraction process comprises subtracting a first subset of the plurality of radiological images from one or more of the plurality of radiological images not in the subset. The digital addition process comprises averaging the received plurality of radiological images.

In some embodiments, the multivariate statistical process comprises combining the plurality of radiological images and removing inter-class dependencies through a multivariate statistical approach.

In some embodiments, the plurality of radiological images are CT images and each of the plurality of CT images are formed by directing, via a first x-ray source, a first x-ray attenuation to an energy integrating detector, wherein the energy integrated detector is dimensioned to produce an image of a predetermined area of the patient, directing, via a second x-ray source, a second x-ray attenuation to a photon counting detector, where the photon counting detector to produce an image of a specific tissue target within the predetermined area; and producing, via a processor, a final CT image based on the image of the predetermined area of the patient and the image of the specific tissue target within the predetermined image.

In some embodiments, the excitation selection process involves selecting a particular radiological image of the plurality of radiological images based on the tissue type.

In another aspect, the invention includes a hybrid computerized tomography (CT) scanner. The hybrid CT scanner can include a first x-ray source that directs a first x-ray attenuation to an energy integrating detector, wherein the energy integrated detector is dimensioned to produce an image of a predetermined area of a patient. The hybrid CT scanner can also include a second x-ray source that directs a second x-ray attenuation to a photon counting detector, where the photon counting detector to produce an image of a specific tissue target within the predetermined area. The hybrid CT scanner can also include a processor to produce a final CT image based on the image of the predetermined area of the patient and the image of the specific tissue target within the predetermined image.

In some embodiments, the energy integrating detector and the photon counting detector are positioned to interrogate the same field of view. In some embodiments, the image of a predetermine area of a patient is a grayscale CT image. In some embodiments, the image of the specific tissue target within the predetermined image is a spectral CT image. In some embodiments, the energy integrating detector relative to its first x-ray source is positioned at a 90 degree difference between the photon counting detector and its second x-ray source.

In some embodiments, the processor is configured to analyze tissue types, the analysis comprising selecting a process among a plurality of processes to analyze the final CT image based on an expected soft tissue type, and segmenting the processed final CT image to display the soft tissue.

In some embodiments, the photon counting detector comprises multiple energy bins that are configured to image a specific tissue target.

In another aspect, the invention involves a computerized method for determining and displaying mixed tissue types.

The method can involve receiving, via a computing device, a radiological image of a patient. The method can involve determining, via the computing device, a first tissue type in a region of interest based on the radiological image of the patient, wherein the first tissue type is a represented by a grid of points across the region of interest. The method can involve determining, via the computing device, a second tissue type, in the region interest based on the radiological image of the patient, wherein the second tissue type is a focal region in the region of interest, wherein at least some of the grid points of the first tissue type coincide in position with the second tissue type.

In some embodiments, the plurality of radiological image are computerized tomography (CT) images, Magnetic Resonance (MR) images, or ultrasound images. In some embodiments, the first tissue type and the second tissue type are overlaid when displayed. In some embodiments, the grid of points has varying densities.

In some embodiments, the first tissue type is micro calcification, and the second tissue type is LNRC, dense calcification, or IPH.

In some embodiments, the method involves performing, via the computing device, multiple energy photon-counting K-edge subtraction imaging on the CT images, performing, via the computing device, spectral image denoising with regularization models on the CT images, improving the signal to noise ratio, via the computing device, of the calcium on the k-edge subtracted and de-noised CT images, and segmenting, via the computing device, the improved calcium images to represent one or both of focally dense calcification and distributed microcalcification.

BRIEF DESCRIPTION OF THE DRAWINGS

Non-limiting examples of embodiments of the disclosure are described below with reference to figures attached hereto that are listed following this paragraph. Dimensions of features shown in the figures are chosen for convenience and clarity of presentation and are not necessarily shown to scale.

The subject matter regarded as the invention is particularly pointed out and distinctly claimed in the concluding portion of the specification. The invention, however, both as to organization and method of operation, together with objects, features and advantages thereof, can be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

It will be appreciated that for simplicity and clarity of illustration, elements shown in the figures have not necessarily been drawn accurately or to scale. For example, the dimensions of some of the elements can be exaggerated relative to other elements for clarity, or several physical components can be included in one functional block or element.

DETAILED DESCRIPTION

In general, the invention involves systems and methods for soft tissue contrast, characterizing tissue, classifying phenotype, stratifying risk, and/or performing multi-scale modeling aided by multiple energy or contrast excitation and evaluation. The invention can involve application of single vs. multi-phase image acquisitions and can include broad spectrum spectral CT to, for example, assess atherosclerotic plaque tissues in a vessel wall and/or perivascular space.

In general, the invention can involve exploiting differing responses by tissue to multi-energy or spectral image sets using a software approach. The invention can also include a hardware configuration that can further discriminate tissues in clinically relevant ranges. The spectral images obtained via the multi-energy levels and/or a broad spectrum can form the input for one or more algorithms that can improve tissue segmentation.

In some embodiments, the algorithm can include a exploiting a non-linear response to differing tissues by noting that noise can be similar across multiple energies, but that the tissue can be different and applying an averaging technique that can result in a higher signal to noise ratio.

In some embodiments, differing tissues can resolve better in one energy level versus another. In some embodiments, different energies are selected for different tissues. In some embodiments, a non-linear response to differing tissues is exploited using a digital subtraction approach. In some embodiments, differing tissue responses are combined from each of optimal energy levels and inter class dependencies are removed through a multi-variate statistical approach. In various embodiments, each of these foregoing embodiments are applied to hardware configurations that amplify such differences, whether designed based on material composition or other physical phenomenon, to achieve benefit. Examples include tissues differentiated by molecular properties, cellular and molecular milieu, material density distributions, morphological presentation, response to stimuli, etc.

In some embodiments, distributed tissue types are used as overlays on focally organized tissues.

Figure 1:
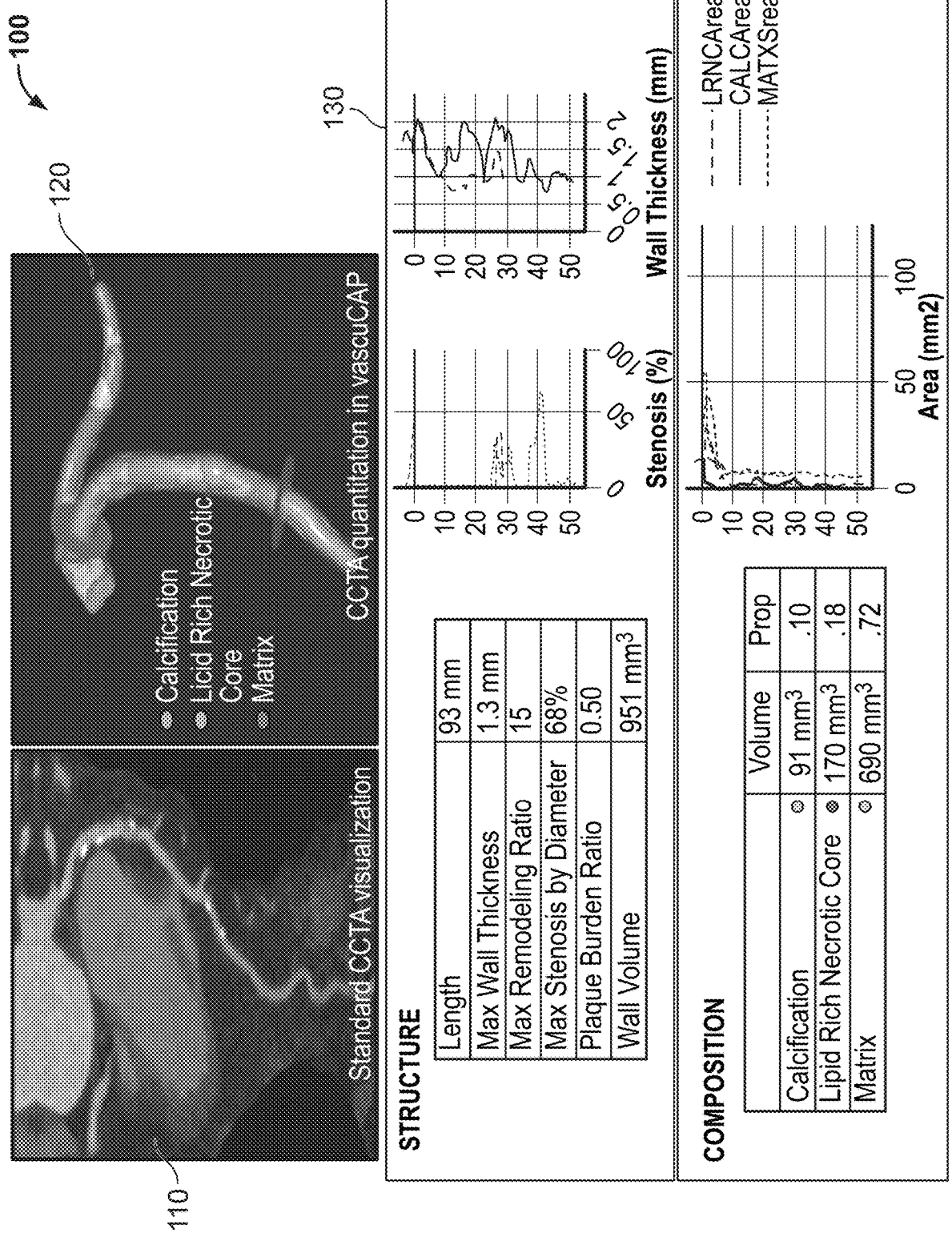
FIG. 1 is a diagram of an example radiological input and processed outputs, according to some embodiments of the invention.

FIG. 1 is a diagram 100 of an example radiological input 110 and processed outputs, according to some embodiments of the invention. The processed outputs can include an image 120 that identifies three-dimensional regions for various measurands of calcification, Lipid Rich Necrotic Core (LRNC) and matrix, and an image 130 that presents tables and graphs of data related to the various measurands. As is apparent to one of ordinary skill in the art, the measurands shown in FIG. 1 are examples and other measurands can be included.

Figure 2:
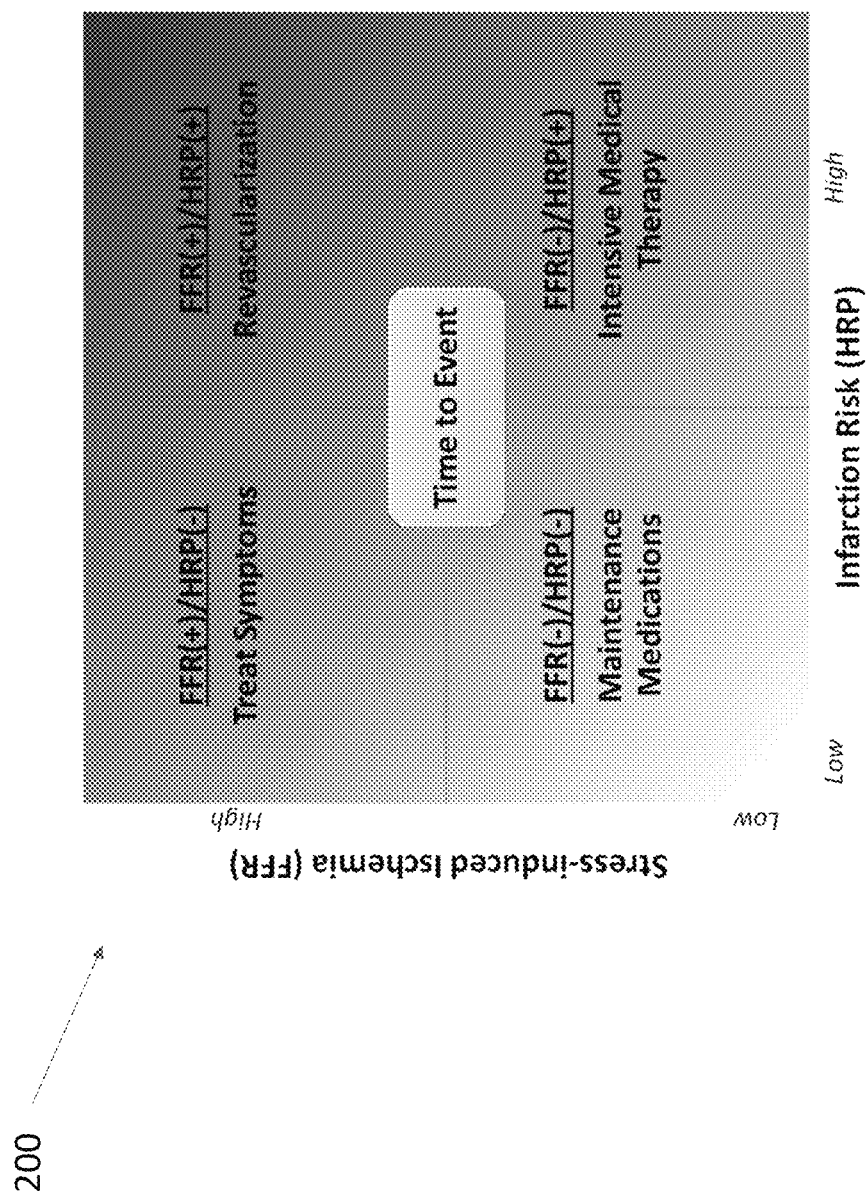
FIG. 2 is a diagram showing an example of atherosclerosis progresses according to common drivers across arterial beds in differing degrees based on evolutionary differences and local factors, according to some embodiments of the invention.

FIG. 2 is a diagram 200 showing an example of atherosclerosis progresses according to common drivers across arterial beds in differing degrees based on evolutionary differences and local factors, according to some embodiments of the invention.

A characterization of coronary artery disease can be accomplished by an assessment of two related but distinct mechanisms: an ability of the arterial system to meet demand under stress, stress-induced ischemia (measured, for example, as FFR or iFR), which can require the delivery of more oxygenated blood to downstream perfused tissues; and a propensity of plaque to physically disrupt or embolize, Infarction Risk (HRP). Therapeutic pathways can be selected optimally based on processed outputs (e.g., processed outputs as described above in FIG. 1 and further below) to characterize a degree to which each of the distinct mechanisms are present, for example, whether one but not the other, neither, or both, at various levels of magnitude. In some embodiment, a likelihood of the conditions, low vs. high, is used to predict a time until an adverse event may take place at the individual patient level. A recommendation for based on an FRR/HRP ratio can be made. The recommendation can be based on the likelihood of the conditions and can include provide maintenance medications, intensive medical therapy, treat symptoms, or revascularization.

In some scenarios, it can be desirable to identify tissue types with complex cellular or molecular level milieu (e.g., complex tissues) that manifests as overlapping material densities. Current methods can be erroneous and fail to correctly identify the tissue types. Current method can include simple thresholding of material density as given by voxel Hounsfield units (HUs). For example, LRNC or idiopathic pulmonary hemosiderosis (IPH) may not easily and/or reliably identified, and/or biological processes that produce them and/or that are triggered in response to them can be complex. LRNC can be variously composed of lipid deposits, cholesterol crystals, apoptotic cellular debris, macrophages and/or calcifications. IPH can be variously composed of intact and/or ruptured red blood cells, macrophages, hemorrhagic debris, fibrin, cholesterol crystals, and/or calcifications. The complex tissues can present difficulty for systems using a single excitation energy for CT, or characteristics RF profile for MR, heterogeneity of plaque components can be exploited based on differences in the tissues response to the excitation, e.g., how they respond to one energy vs. another, or one radio frequency vs. another, which can respond differently to various energies. Therefore, it can be desirable to relax a strict dependency on material density. In some embodiments, different density distributions can be mathematically fit to exemplars from histopathology to relax a strict dependency on material density.

In some embodiments, applying multiple energy signals during the CT scan and using digital subtraction, averaging, and/or selection techniques to amplify the signal for one tissue type over another, and all over the level of noise can be used to relax a strict dependence on material density. In some embodiments, the HU of adjacent voxels may be analyzed as a distribution rather than only as individual voxels, by maximizing the Mumford-Shah functional, as an exemplary embodiment.

Analogously to the stains which are applied to tissues which assist pathologists exercise judgement when they outline LRNC and IPH, the present invention can be understood as applying "digital stains" to the imagery to accomplish a similar amplification because they are heterogeneous and overlapping tissues are composed of multiple cell types, with differing densities, each responding differently to differing incident energy. Pathology annotation takes this into account as pathologists mark tissue boundaries of LRNC and IPH on CTA need to be established using similar judgment to what pathologists do on histology so that clinical insights based on it apply. This requires more than just applying HU thresholds. It requires a mathematical formalism that can be used to mimic the judgment used by human pathologists trained in recognizing tissue.

Figure 3:
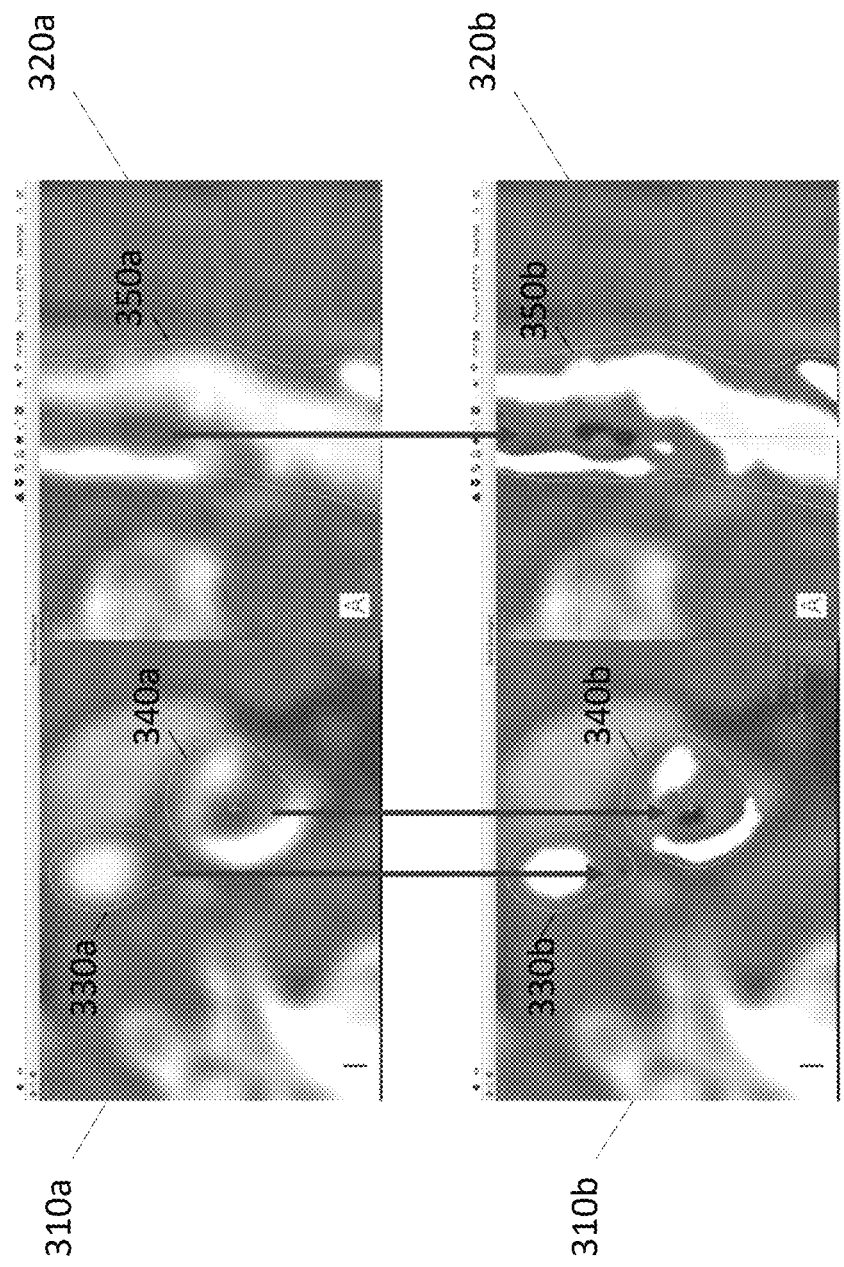
FIG. 3 is an example of a first set of CT scan and a second set of CT scan that shows an improved soft tissue contrast, according to some embodiments of the invention.

MRI, ultrasound, nuclear medicine, and/or other imaging modalities can be reconstructed with various strengths and weakness prior to post-processing. FIG. 3 is an example of a first set of CT scans 310a, 320a and a second set of CT scans 310b, 320b that shows an improved soft tissue contrast, according to some embodiments of the invention. One CT scan 310a in the first set of CT scans shows two regions 330a and 340a that are improved in a CT scan 310b of the second set of CT scans as seen in 330b, 340b. One CT scan 320a is the first set of CT scans shows one region 350a that is improved in a CT scan 320b of the second set of CT scans as seen in 350b.

Figure 4:
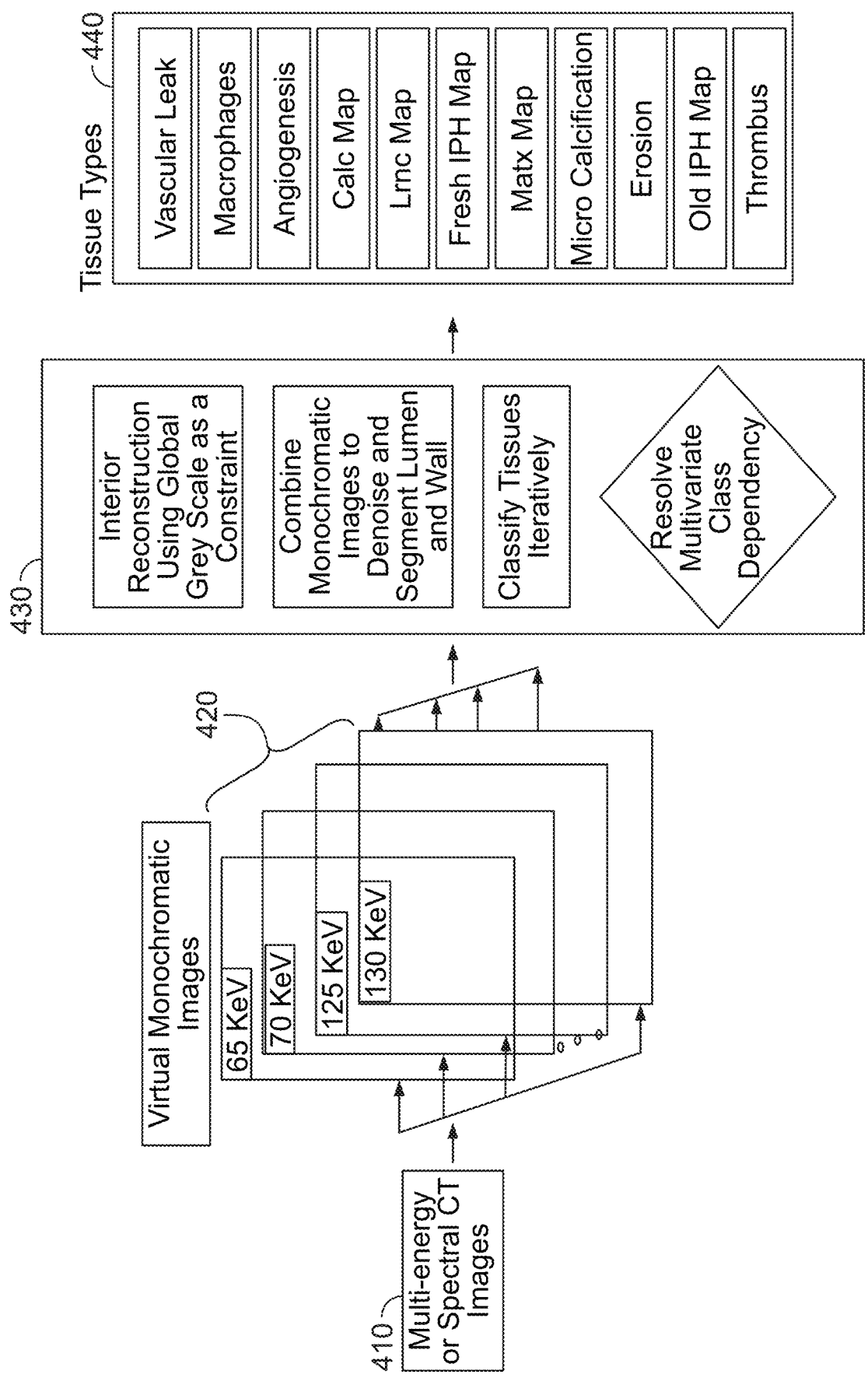
FIG. 4 is a diagram of a system for improving soft tissue segmentation, according to some embodiments of the invention.

FIG. 4 is a diagram of a system for improving soft tissue segmentation, according to some embodiments of the invention. The system can include an imaging device 410, a classification unit 430.

The imaging device 410 can be a CT scanner, Magnetic Resonance Imaging, Ultrasound, and/or other imaging devices as are known in the art. The imaging device 410 can obtain one or a plurality of radiological images (e.g., CT, MR, Ultrasound) 420. The plurality of radiological images 420 can be monochromatic. The plurality of monochromatic images 420 can be taken at a plurality of excitations. As is apparent to one of ordinary skill in the art, a plurality of images taken at a plurality of excitations can be as a result of transmission, a reception, or any combination thereof.

The plurality of excitations can include a plurality of energies, radio frequencies pulses (e.g., sequences), and/or differing frequencies or timings, as used by CT, MRI, and/or ultrasound, respectively. In some embodiments, each of the plurality of monochromatic images 420 are taken at a unique excitation (e.g., unique x-ray energy, whether as transmitted, as received, or both, and as a narrow energy range, or as a broader range) of a CT scanner, unique pulse sequences for an MRI, unique frequencies and/or timings for ultrasound).

A number of the plurality of monochromatic images 420 can depend on what type of tissues or phenotypes that are desired to be discriminated.

In some embodiments, some of the plurality of monochromatic images 420 are taken at the same excitations and others of the plurality of monochromatic images 420 are taken at different excitations. For example, each time two monochromatic images 420 are taken, the excitation can change. In another example, just the first two monochromatic images 420 are the same excitation and the remaining monochromatic images 420 are taken at a unique excitation. As is apparent to one of ordinary skill in the art, plurality of monochromatic images 420 can include any combination of the same and unique excitations.

The excitation can be dependent upon a type of tissue expected. For example, for an expected tissue type of calcium and a CT imaging device, the excitation (whether as transmitted, as received, or both) can be 4 keV. In another example, for an expected tissue type of oxygen and a CT imaging device, the excitation (whether as transmitted, as received, or both) can be 530 eV.

In the example shown in FIG. 4, the plurality of monochromatic images 420 are shown as taken with a CT imaging device and a excitation (whether as transmitted, as received, or both) at an exemplary range of 65 KeV to 130 KeV, but can go as low, for example, 0.5 keV or as high as 400 keV, depending on the tissues of interest, such spectra allow discrimination of tissue types identified as 440 among others.

The classification unit 430 can include a plurality of processes to analyze the plurality of monochromatic images 420. The plurality of processes can include a digital subtraction process, digital addition process, a multivariate statistical process, and/or an excitation selection process, as described in further detail below with respect to FIG. 5. The classification unit 430 can output data 440 indicative of one or more classified tissue types (e.g., segmented image data for tissue types, and/or other data as shown above in FIG. 1).

The output data 440 can be classified tissue types of vascular leak, macrophages, angiogenesis, CALC map, LRNC map, FRESH IPH map, MATX map, Micro Calcification, erosion, OLD IPH map, thrombus, or any combination thereof. As is apparent to one of ordinary skill in the art, the output data can be tissue types as are known in the art.

Figure 5:
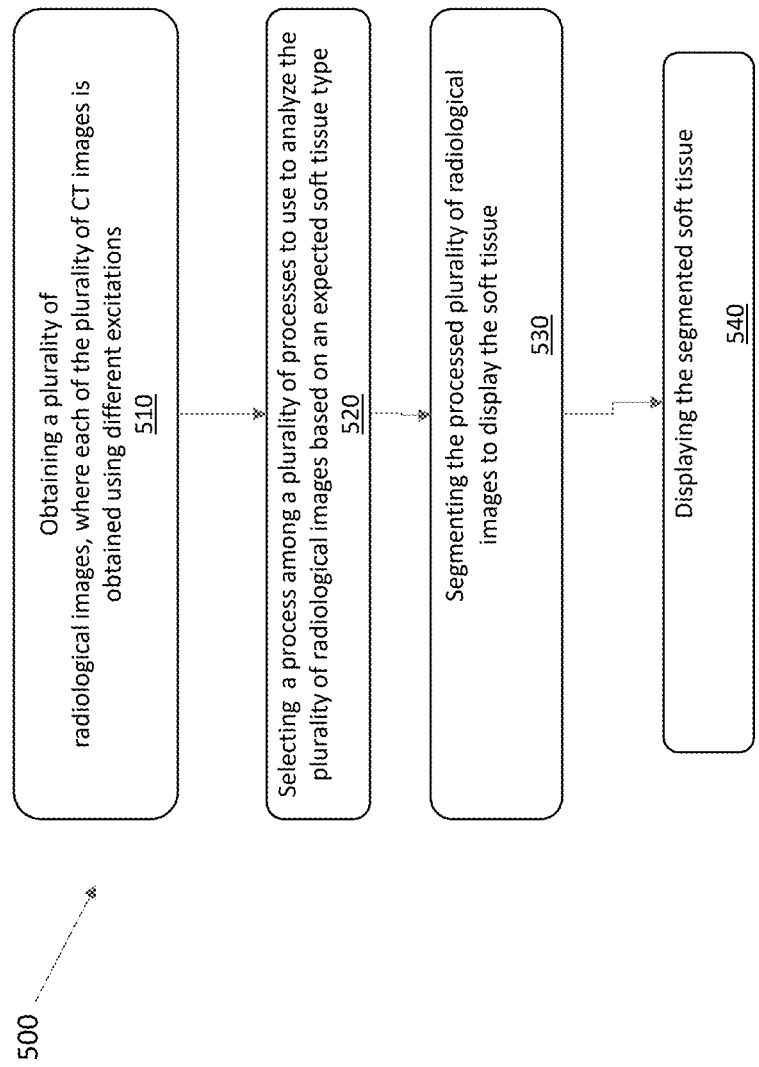
FIG. 5 is an example of a method for improving soft tissue segmentation, according to some embodiments of the invention.

FIG. 5 is an example of a method 500 for improving soft tissue segmentation, according to some embodiments of the invention. The method can involve obtaining a plurality of radiological images (e.g., CT images, MRI images, ultrasound images). The radiological images can be obtained via a hybrid CT imaging device as described below in FIG. 6. Each of the plurality of radiological images can be obtained using different excitations (Step 510).

In some embodiments, the plurality of radiological image are CT images and the different excitations are different x-ray energy (whether as transmitted, as received, or both, and as a narrow energy range, or as a broader range). In some embodiments, the plurality of radiological image are MR images and the different excitations are different radio frequency pulses. In some embodiments, the plurality of radiological image are ultrasound images and the different excitations are different frequencies.

The method can involve selecting a process among a plurality of processes (e.g., via the classification unit 430) to analyze the plurality of radiological mages based on an expected soft tissue type (Step 520). The plurality of processes can include a digital subtraction process, digital addition process, a multivariate statistical process, and/or an excitation selection process.

The selection of the process among the plurality of processes can be random, input by a user, and/or based on the characteristics of the tissue.

The digital subtraction process can involve taking one of the plurality of radiological images image at one spectral range and subtracting it from another of the plurality of radiological images. In some embodiments, the digital subtraction can involve subtracting a first subset of the plurality of radiological images from one or more of the plurality of radiological images not in the subset. In some embodiments, the digital subtraction process can involve subtracting a narrow range from a broad one, for example to cause a narrow band signal to be raised above a broad band noise floor. In some embodiments, the digital subtraction process can involve subtracting subtract one medium bandwidth from another medium bandwidth, to distinguish two related tissue types.

The digital addition process can involve averaging the plurality of radiological images. Averaging the plurality of radiological images can be advantageous due to noise typically being similar across energies, whereas the tissue signal is not, such that averaging can result in a higher signal to noise ratio.

The multivariate statistical process can involve combining each of the plurality of radiological images with a mathematical operator other than simple subtraction or addition and removing any inter-class dependencies through a multi-variate statistical approach from the set of techniques identified as non-linear operators.

The excitation selection process can involve selecting one or a subset of radiological image of the plurality of images for a particular tissue type, as certain tissue types can resolve better in one energy level or a subset of energy levels. For example, the energy dependence of a tissue might be at a stable point at higher kVp levels or lower, and for another tissue at another range, suggesting usage of the one range for one tissue, vs. the other tissue.

The processed plurality of radiological images can be input to one or more classification models. In some embodiments, the classification models may be trained as described in U.S. Pat. No. 11,094,058, filed on Nov. 28, 2018, incorporated herein by reference in its entirety.

The method can also involve segmenting the processed plurality of radiological images to display the soft tissue (Step 530). In some embodiments, segmenting processed plurality of excitations further comprises segmenting the medical image data into three-dimensional (3D) objects.

In some embodiments, segmenting the processed plurality of radiological images includes segmenting the processed plurality of radiological images into an outer wall boundary. In some embodiments, the segmentation involves segmenting the plurality of radiological images into a lumen and an outer wall based on a segmented lumen boundary, outer wall, perivascular region, and/or focal tissue boundaries. FIG. 4 of U.S. Pat. No. 11,094,058, along with the corresponding description, shows an example of segmentation levels for a multi-scale vessel wall analyte map.

Figure 6:
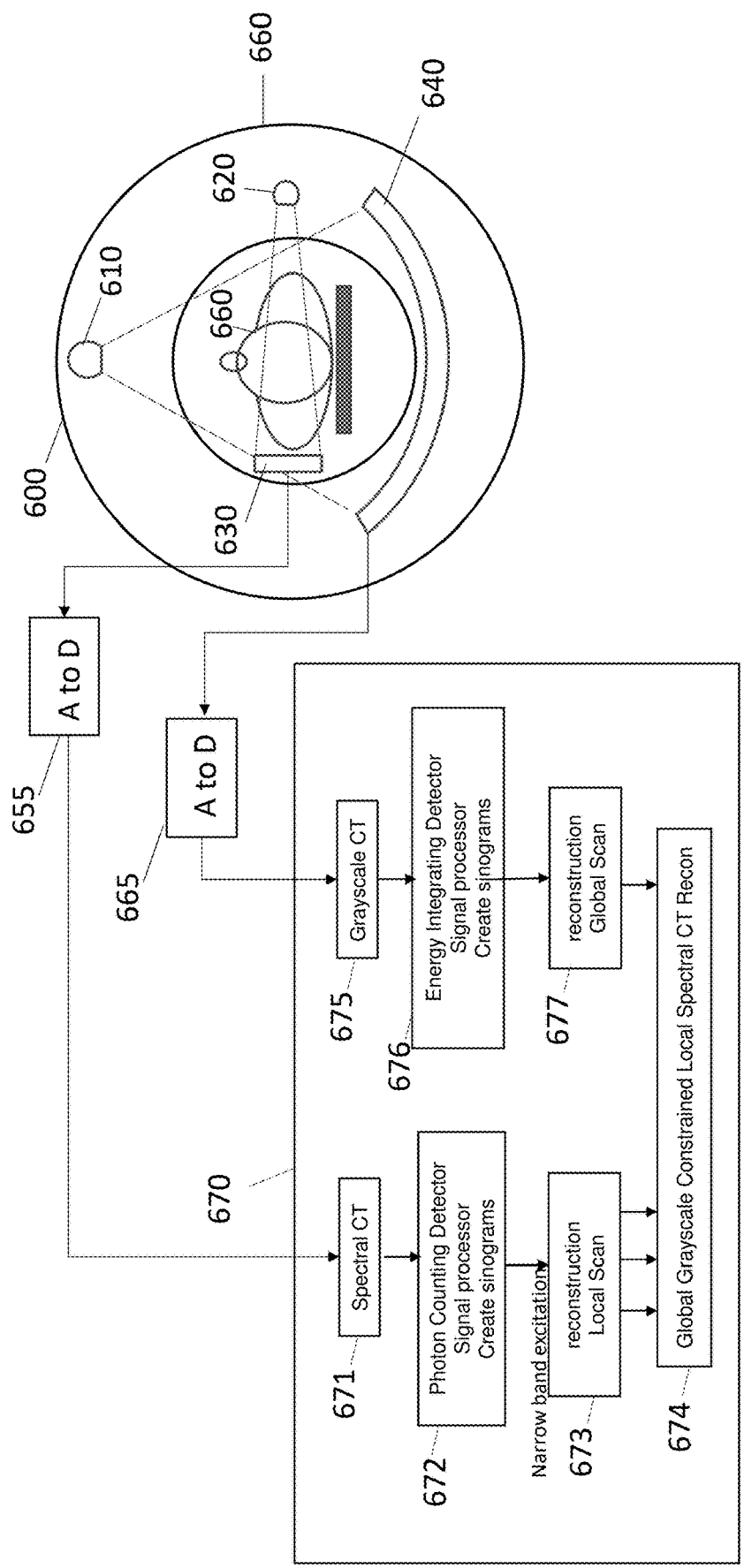
FIG. 6 is a cross-sectional front view of a hybrid computed tomography (CT) scanner, according to some embodiments of the invention.

FIG. 6 is a cross-sectional front view of a hybrid computed tomography (CT) scanner 600, processor 670, and two analog to digital converters 655 to 665, according to some embodiments of the invention. The hybrid CT scanner 600 can provide a truncated spectral scan and/or a local reconstruction constrained with global grayscale image from a conventional CT configuration.

The hybrid CT scanner 600 includes a first x-ray source 610, a second x-ray source 620, a photon counting detector 630, an energy integrating detector 640, a gantry 650. The energy integrating detector 640 can be positioned relative to the first x-ray source 610 at predetermined angle between the photon counting detector 630 and the second x-ray source 620. As shown in FIG. 6, the predetermined angle is ~90 degrees. The predetermined angle can be based on optimizing a physical space around an arc to allow the integrating detector to have wide coverage.

The first x-ray source 610 and/or the second x-ray source 620 can be polychromatic x-ray sources. The first x-ray source 610 and/or the second x-ray source 620 can be any x-ray source as is known in the art to be used with CT scanners.

During operation, a patient 660 is inserted into the hybrid CT scanner 600 and the first x-ray source 610 can direct a first x-ray attenuation towards the patient 660 and the energy integrating detector 640. The energy integrated detector 640 can be dimensioned to produce an image of a predetermined area of the patient 660.

The energy integrated detector 640 can have a curvature defined by a radius R and a diameter D and extend along an arc A, such that a predetermined area of the patient is imaged. For example, the radius R can be 30 inches, the diameter D can be 60 inches, and the arc A can be 135 degrees.

In some embodiments, the first x-ray attenuation is transmitted at a range of 65 to 130 keV, or wider.

The energy integrating detector 640 receives at least a portion of the first x-ray attenuation and energy that has transmitted through the patient 660.

The second x-ray source 620 can directs a second x-ray attenuation towards the patient 660 and the photon counting detector 630. The photon counting detector 630 can produce an image of a specific tissue target within the predetermined area.

In some embodiments, the second x-ray attenuation is transmitted at range similar than the first or different.

The photon counting detector 630 receives at least a portion of the second x-ray attenuation and energy that has transmitted through the patient 660.

The energy integrating detector 640 and the photon counting detector 630 communicate their respective received energy to the processor 670 via the a/d converters 655, 665.

It has been known that the compressive sensing-based reconstruction algorithms can be used to exactly reconstruct an region of interest if an object is piecewise constant. TV-minimization-based spectral interior reconstruction will find important applications in CT field, such as dose reduction, fast data acquisition, easy data storage and hardware cost-reduction. To avoid the assumption made by many reconstruction schemes that assume a condition where the object imaged is piece-wise constant, which is not commonly satisfied in clinical CT imaging due to tissue composition and/or contrast medium with gradient density appreciably less than a voxel scale, we use a global energy-integrating image to facilitate the interior spectral CT reconstruction and minimize the reconstruction errors due to significant data truncations using processer 670.

The processor 670 receives the outputs from the energy integrating detector 640 and the photon counting detector 630 and processes the images to produce a final CT image based on the image of the predetermined area of the patient and the image of the specific tissue target within the predetermined image. The final CT image can be used as an input to the processes as described above in FIG. 5.

The processor 670 can include multiple processing modules. The processing modules can include a module 671 to receive the spectral CT from the a/d converter 655 from the photon counting detector 630. Spectral CT can be transmitted to the photon counting detector signal processor module 672 to create sinograms. The sinograms are transmitted to the local scan module 673 to perform reconstruction. The module 675 can receive the grayscale CT from the a/d converter 675 from the energy integrating detector 640. The grayscale CT can be transmitted to the energy integrating detector processor module 676 to create sinograms. The sinograms are transmitted to global scan module 677 to perform reconstruction. The output (e.g., a narrowband output) of local scan module 673 and the output (e.g., multiple energy output that can interrogate more energies than the local scan, (e.g., multiple narrow outputs or a single wideband output) of the global scan module 677.

As is known in the art the processing modules on processor 670 can be implemented in one processor or multiple processors.

The energy integrated detector 640 can be viewed as a global scan of the patient 660 while the photon counting detector 630 can be viewed as a local scan. The CT images from energy integrating detector 640 can be used for a standalone CT reconstruction or as used as global grayscale constraint for an interior spectral CT local tomography reconstruction using photon counting detector 630. The photon counting detector 630 can include multiple energy bins that are configured to image a specific tissue target, multiple channels of reconstructed global grayscale constrained spectral images can be used to present and differentiate tissue.

An interior spectral CT reconstruction using grayscale image as a global constraint can be determined as follows:

Assume N is the number of spectrum channels (e.g., number of plurality of energies or tube voltages of the CT images, $I_i$ is a photon intensity of a specific spectrum channel, and i is channel index. A projection image of energy-integrating can be written as:

$$G = \sum_{i=1}^{N} I_i \exp(-\int \mu_i(r) dr) \quad \text{EQN. 1}$$

where $\mu_i(r)$ for a specific spectral channel can be expressed as an attenuation decomposition from grayscale template, as follows:

$$\mu_i(r) = \mu_{gray}(r) + \delta\mu_i(r) \quad \text{EQN. 2}$$

where $\mu_{gray}(r)$ Attenuation map reconstructed from energy-integrating projection.

$$G = \sum_{i=1}^{N} I_i \exp(-\int [\mu_{gray}(r) + \delta\mu_i(r)] dr) \quad \text{EQN. 3}$$

i.e.

$$G = \sum_{i=1}^{N} I_i \exp(-\int \mu_{gray}(r) dr) \exp(-\int \delta\mu_i(r) dr) \quad \text{EQN. 4}$$

Assume that $\delta\mu_i(r)$ is small enough using Tailor series expansion and ignoring high-order terms, results in:

$$G = \sum_{i=1}^{N} I_i \exp(-\int \mu_{gray}(r) dr)[1 - \int \delta\mu_i(r) dr] \quad \text{EQN. 5}$$

Assume $C = \exp(-\int \mu_{gray}(r) dr)$ and substitute it in EQN. 5, results in:

$$G = \sum_{i=1}^{N} I_i C [1 - \int \delta\mu_i(r) dr] \quad \text{EQN. 6}$$

It should be noted that $$G = \sum_{i=1}^{N} I_i C \quad \text{EQN. 7}$$

Suppose that there are three channels: N=3; The following equations follow:

$$I_1 C \int \delta\mu_1(r) dr + I_2 C \int \delta\mu_2(r) dr + I_3 C \int \delta\mu_3(r) dr = I_1 C + I_2 C + I_3 C - G = 0 \quad \text{EQN. 8}$$

$$B_i = I_i \exp(-\int [\mu_{gray}(r) + \delta\mu_i(r)] dr) \quad \text{EQN. 9}$$

From $B_i = I_i \exp(-\int \mu_{gray}(r) dr) \exp(-\int \delta\mu_i(r) dr)$, the results the linear inverse equations as follows:

$$\begin{cases} I_1 C \int \delta\mu_1(r) dr + I_2 C \int \delta\mu_2(r) dr + I_3 C \int \delta\mu_3(r) dr = 0 \\ \int \delta\mu_1(r) dr = -\ln\left(\frac{B_1}{I_1 C}\right) \\ \int \delta\mu_2(r) dr = -\ln\left(\frac{B_2}{I_2 C}\right) \\ \int \delta\mu_3(r) dr = -\ln\left(\frac{B_3}{I_3 C}\right) \end{cases} \quad \text{EQNS 10-14}$$

Where N is a total number of spectrum channels, I is Photon intensity emitted from x-ray source. $I_i$ is Photon intensity at a spectral channel, i: spectral channel index; μ is attenuation map to be reconstructed, B is Photon intensity detected from a spectral channel, G is grayscale photon intensity detected, r is spatial position in a 3D space; δ is small variation and exp (x) is exponential function.

Figure 7A:
FIG. 7A shows an example of multi-scale association linking radiology scale plaque morphology to molecular determinants, according to some embodiments of the invention.

FIG. 7A shows an example of multi-scale association linking radiology scale plaque morphology to molecular determinants, according to some embodiments of the invention. Prediction-based scoring, for example, including the validation of surrogate markers, may use (1) for dynamic vessel performance, examples including performance at hyperemia (e.g., causative of ischemia) and/or rupture risk (e.g., causative of infarction) (2). Quantitation of morphology measurands, including for example but not limited to IPH, include analysis of modalities, for example including single-energy CTA, or multi-spectral CTA (3). Fluid-dynamics, e.g., shear stress assessment and finite element models (FEM) may elucidate mechanical triggers for smooth muscle cell differentiation (SMC) differentiation (4), underpinning (2).

Figure 7B:
FIG. 7B is an example of multi-scale modeling, according to some embodiments of the invention.

FIG. 7B is an example of multi-scale modeling, according to some embodiments of the invention. In FIG. 7B x represents a predisposition and/or expression (e.g., characterizing tissue) of cellular and/or molecular level species, y represents macro-molecular tissue presentation which may be assayed by radiology and/or used to classify phenotype, and z represents predicted outcomes (e.g., stratifying risk), simulated progression, and/or simulated regression under differing classes of therapy. If x and y are known, they may be used to train models, generate hypotheses, and/or provide a base for simulation. If x is known but not y, or vice versa, prediction models can be utilized if trained with examples where both x and y are known. One example purpose can be to provide means that may be practically and/or economically easier to perform clinically to obtain information across scales.

In some embodiments, a causal relationships can be analytically established such as, does x cause y, and/or, if we see y, can the mechanisms at the level of x plausibly create y be identified. In some embodiments, a utility for such analyses includes if knowing x changes what specific drug or surgical intervention can be optimal, then treatment can be personalized.

In some embodiments, analytic methods can be used to establish whether the relationship between x and y may be spatially differentiated to determine, for example, if the specificity may increase diagnostic confidence by aboding dilution that occurs as a result of not accounting for spatial context, analogous to the value of single cell techniques relative to techniques that do not provide differentiation.

Figure 7C:
FIG. 7C is an example of expanded multi-scale modeling, according to some embodiments of the invention.

FIG. 7C is an example of extended multi-scale modeling, according to some embodiments of the invention. Extending the multi-scale modeling techniques, x, y, and z can include adding time-dependent functions. For example, x(t) can capture plaque development, e.g., by premature aging, and/or other mechanistic explanations at cellular/molecular level, y(t) can capture macroscopic phenotyping observed at radiology over time, and z(t) can predict what happens next under candidate treatment plans (e.g., including if left untreated). In some embodiments, the analyses provide y(t) as 3D objects validated at histology, for a spatially-resolved basis at the macroscopic level and/or also manifest in convolutional neural networks for phenotype classification. To connect to molecular/cellular level, literature may be mined, and tissue resources may be used to augment with de novo experiments for data collection.

Figure 8:
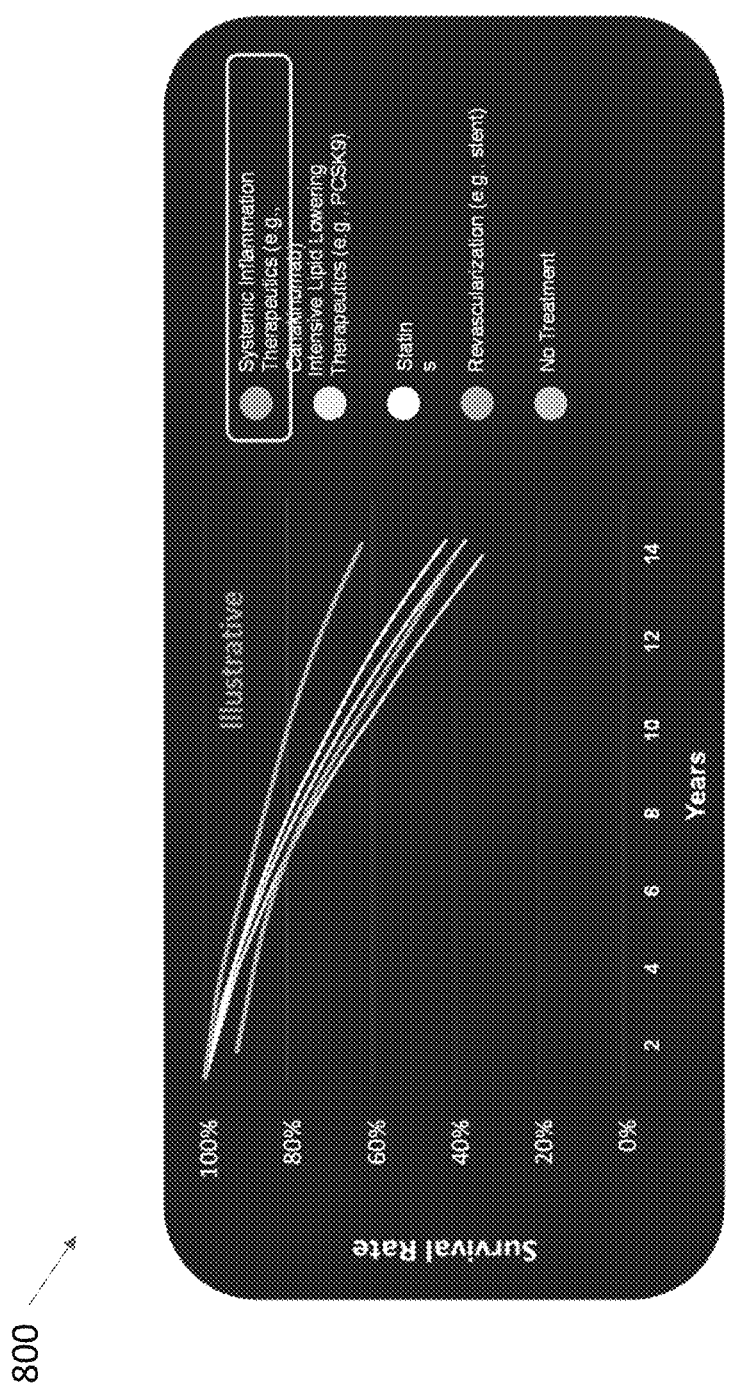
FIG. 8 is an example output screen showing multiple simulated event-free survival possibilities under untreated and under various treatment scenarios, according to some embodiments of the invention.

FIG. 8 is an example output screen 800 showing multiple simulated event-free survival possibilities under untreated and under various treatment scenarios, according to some embodiments of the invention. The simulated even-free survival possibilities include systemic inflation therapeutics 810, intensive lipid lowering therapeutic 820, Statin s 830, Revascularization (e.g., stent) 840, and no treatment 850.

Whether obtaining CT scans with single energy or multiple energy, complex tissue presentations (e.g., tissues in a region that include more than one tissue type in certain locations) can be identified. For example, a complex tissue region can be microcalcification over MATX, or over LRNC, etc. Adaptive grid sizing and/or adaptive region growing can be used to create nuanced representations of complex tissue types. Complicated biology can be represented as a screen overlay or a grid point overlay and can determine the progression of the complicated biology, not only the end results. For example, progression of microcalcification can be determined, not only an end result of dense macrocalcification.

Such screens or grid point overlays typically do not replace focal tissue presentations but can augment them. Continuing with the microcalcification example, the subjective parlance has used the term "spotty calcification," but this parlance can fail to represent intermediate signs of focal organization. In some embodiment, intermediate signs of focal organization of microcalcification can be visually represented as a "grid overlay" that represents points, either sparse or dense (e.g., not material density, but point density) to show a pattern of organization.

The grid overlay can be represented for the purpose of helping human observers to visualize in the software as a "texture" and/or can be represented on data objects that are well suited to computer processing as a "mottling." In this manner, the tissue organization can affect not only MATX, but also LRNC and/or other tissue regions also. Like IPH, micro-calcification can be subdivided into two tissue/stage types: dense and/or early stage. Microcalcification can be a grid, whereas dense macrocalcification can be focal. The microcalcification grid can be interpreted as a distribution of niduses which can generalize how tissue is represented capable of expressing transitional states where the niduses collect. For example, not all the way to dense yet but getting closer. Tissue types of vascular leak, microcalcification, angiogenesis can be represented as grids of varying point densities. Tissue types expressed as focal regions like LRNC, CALC, and IPH can be focal regions. MATX can be expressed as a focal region, but with regions that are better described as other tissues.

Figure 9:
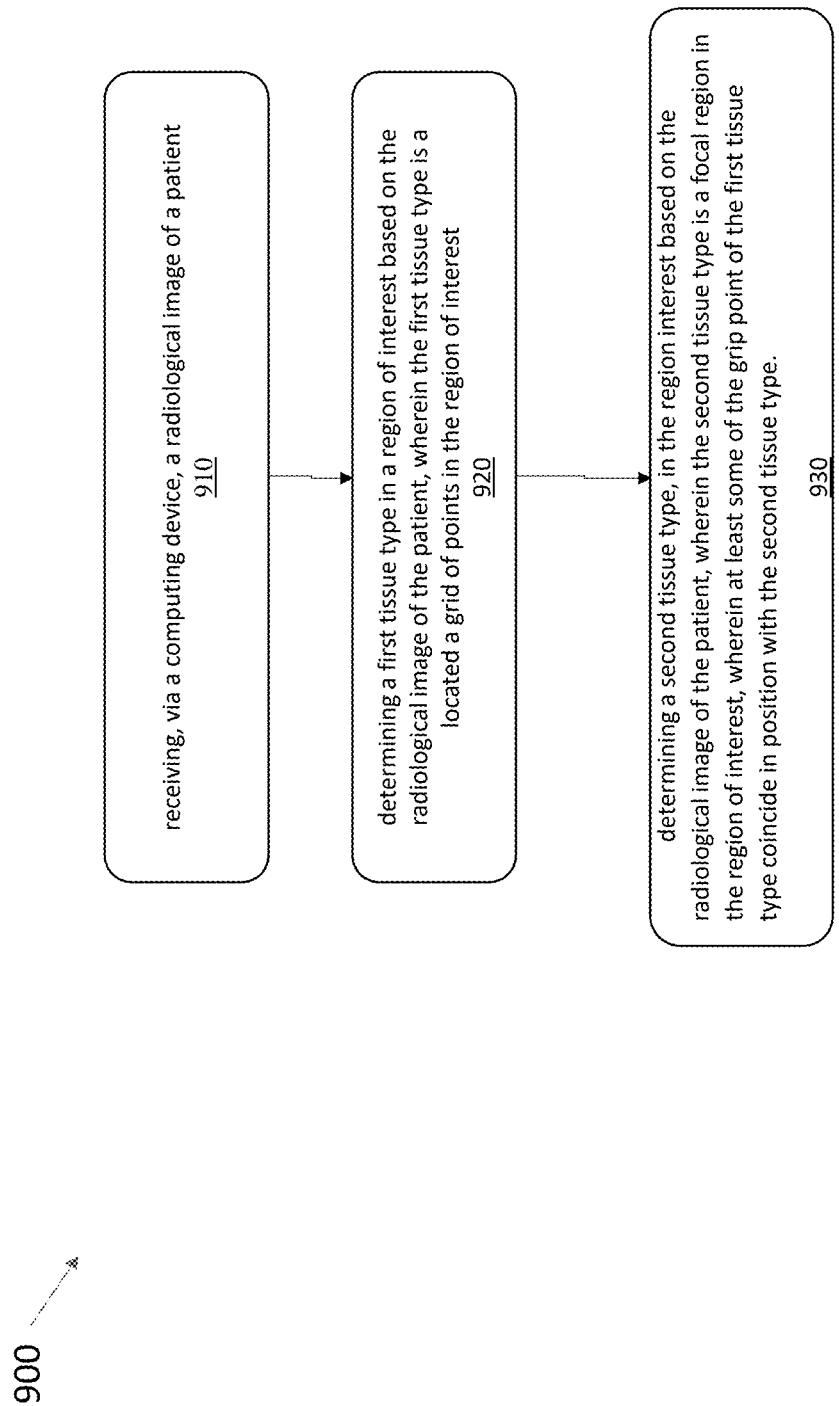
FIG. 9 shows a method for determining and displaying mixed tissue types, according to some embodiments of the invention.

FIG. 9 shows a method 900 for determining and displaying mixed tissue types, according to some embodiments of the invention.

The method can involve receiving a radiological image of a patient (Step 910). The radiological image can be a CT image, MR image or an ultrasound image. For a radiological image of a CT image, the CT image can be obtained using the hybrid CT imaging device as described above in FIG. 5

The method can involve determining a first tissue type in a region of interest based on the radiological image of the patient, wherein the first tissue type is a grid of points in the region of interest (Step 920). For example, the first tissue type can be any tissue type that can progress from less to more dense. The first tissue type can be any tissue type that can be dispersed on another tissue type. The first tissue type can be vascular leak, microcalcification and/or angiogenesis.

The grid of points can be each be represented as point densities. Each point on the grid of points can have some of the same, all of the same, or unique density values.

The first tissue type can be determined via the system above in FIG. 4, the method shown above in FIG. 5, the system above in FIG. 6, or any combination thereof.

The method can involve determining a second tissue type, in the region interest based on the radiological image of the patient, wherein the second tissue type is a focal region in the region of interest, wherein at least some of the grip point of the first tissue type coincide in position with the second tissue type (Step 930). The second tissue type can be any tissue type that can be expressed as a focal region. The second tissue type can be LRNC, CALC, and/or IPH.

The second tissue type can be determined via the system above in FIG. 4, the method shown above in FIG. 5, the system above in FIG. 6, or any combination thereof.

Figure 10:
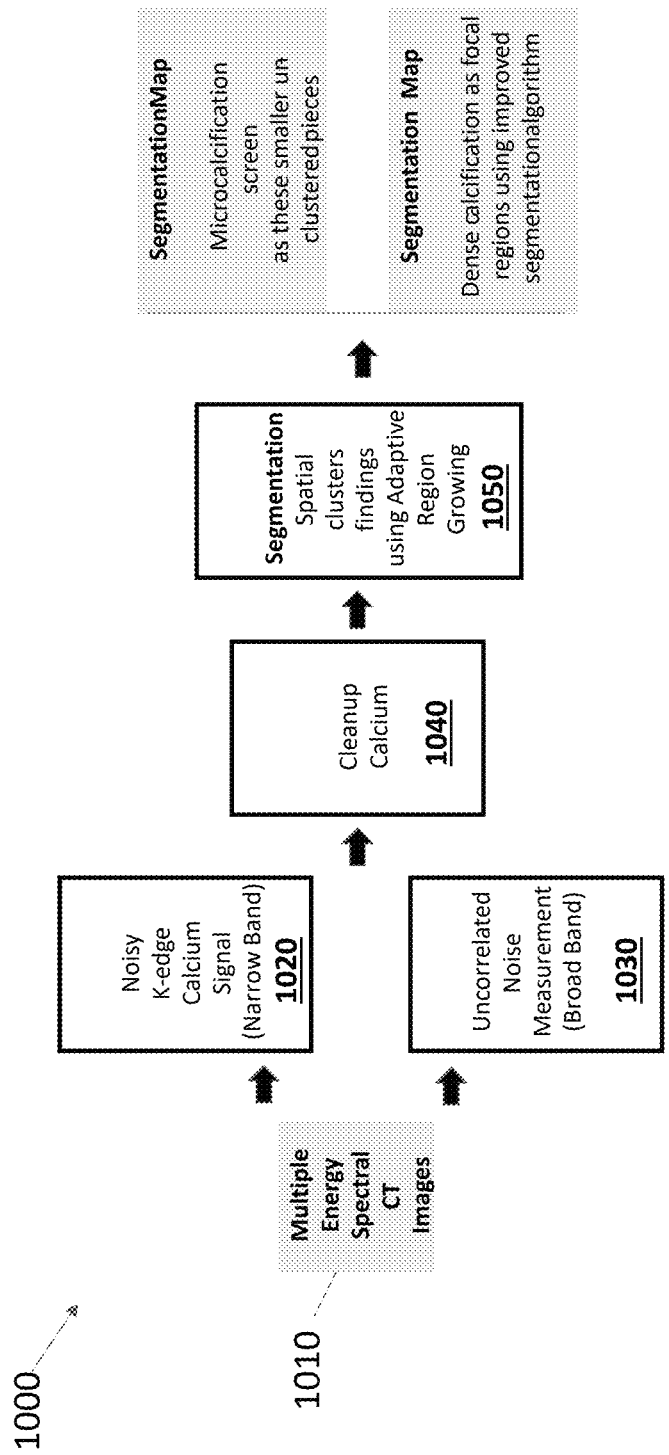
FIG. 10 shows a method for determining and displaying mixed tissue types of a microcalcification screen and dense calcification regions using radiological images of multiple energy spectral CT images, according to some embodiments of the invention.

FIG. 10 shows a method 1000 for determining and displaying mixed tissue types of a microcalcification screen and dense calcification regions using radiological images of multiple energy spectral CT images, according to some embodiments of the invention.

The method involves receiving multiple energy spectral CT images (e.g., via the system of FIG. 4 as describe above) (Step 1010).

The method can involve performing multiple energy photon-counting K-edge subtraction imaging (1020). In some embodiments, for K-edge decomposition imaging for the multiple-energy system with the photon counting detectors (PCDs), energy bins can significantly affect an intensity of the extracted K-edge signal to provide optimized energy bins with the potential to improve classifications between micro-calcifications and focal/dense calcifications.

The method can involve performing spectral image denoising with regularization models (1030). In some embodiments, linear attenuation coefficient maps are decomposed into basis materials separable in spectral and space domains. Nonlinearities can be converted to the reconstruction of mass density maps. The dimensionality of the optimization variables may be reduced and/or a minimization scheme whereby the reconstruction is solved with regularizations of weighted nuclear norm and total variation, thus providing more spectral information with reduce noise.

The method can involve improving (e.g., cleaning) up the calcium (Step 1040) by subtracting A from B to, for example, effectively improving the signal to noise ratio.

The method can involve segmenting the improved calcium (Step 1050). The segmentation can result in a dense calcification focal region and a microcalcification screen (e.g., grid overlay).

In some embodiments, principal component analysis (PCA) for feature extraction is used with spectral imaging to extract a small HU difference of soft tissues presented in multiple energy images. Soft tissues can be extracted by, for example, using adaptive region growing and K-means clustering technique. Region growing algorithms can be used to separate regions that have the same properties that predefined a prior and can provide the original images of clear edges with good segmentation results. In some embodiments, stages of segmentation can be as follows: 1) a morphological reconstruction can be applied to smooth the flat area and/or preserve the edge of the image; 2) multiscale morphological gradient can be used to avoid thickening and/or merging of the edges; 3) for contrast enhancement, a top/bottom hat transformation can be used; 4) the morphological gradient of an image can be modified by imposing regional minima at the location of both the internal and the external markers; and 5) a weighted function can be used to combine the top/bottom hat transformation algorithm and the markers algorithm to get the new algorithm. In this manner, over segmentation from traditional watershed can be prevented.

Figure 11:
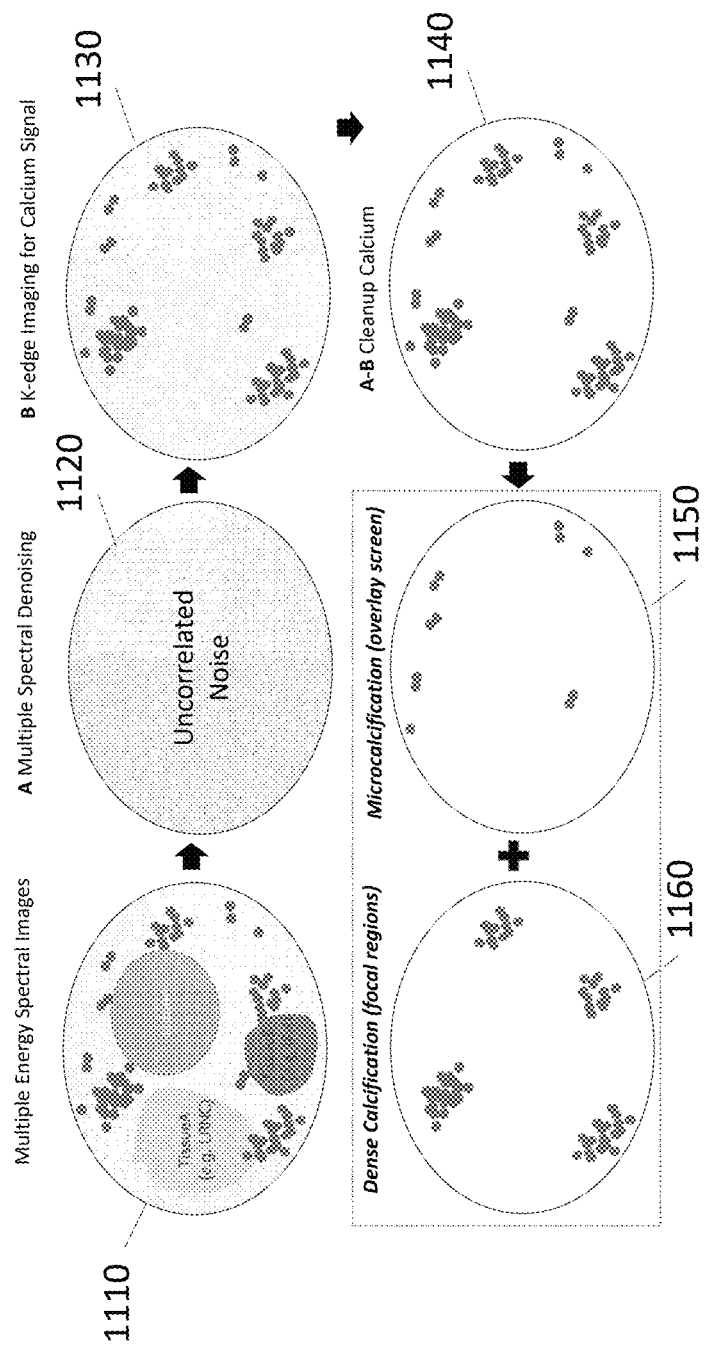
FIG. 11 are diagrams showing examples of the method of FIG. 10, according to some embodiments of the invention.

FIG. 11 are diagrams showing examples of the method of FIG. 10, according to some embodiments of the invention. Diagram 1110 shows the received multiple energy spectral CT images (e.g., Step 1010 as shown above in FIG. 10).

Diagram 1130 shows the output of performing multiple energy photon-counting K-edge subtraction imaging in the CT images (e.g., Step 1020 as shown above in FIG. 10). Diagram 1120 shows the output of performing spectral image denoising with regularization models on the CT images (e.g., Step 1030 as shown above in FIG. 10). Diagram 1140 shows the output of cleaning up the calcium (e.g., Step 1040 as shown above in FIG. 10). Diagrams 1150 and 1160 shows segmenting the cleaned calcium (e.g., Step 1050 as shown above in FIG. 10) into dense calcification 1160 and microcalcification 1150.

Although embodiments of the invention are not limited in this regard, discussions utilizing terms such as, for example, "processing," "computing," "calculating," "determining," "establishing", "analyzing", "checking", or the like, can refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that can store instructions to perform operations and/or processes.

Although embodiments of the invention are not limited in this regard, the terms "plurality" and "a plurality" as used herein can include, for example, "multiple" or "two or more". The terms "plurality" or "a plurality" can be used throughout the specification to describe two or more components, devices, elements, units, parameters, or the like. The term set when used herein can include one or more items. Unless explicitly stated, the method embodiments described herein are not constrained to a particular order or sequence. Additionally, some of the described method embodiments or elements thereof can occur or be performed simultaneously, at the same point in time, or concurrently.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by an apparatus and can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above-described techniques can be implemented on a computer having a display device, a transmitting device, and/or a computing device. The display device can be, for example, a cathode ray tube (CRT) and/or a liquid crystal display (LCD) monitor. The interaction with a user can be, for example, a display of information to the user and a keyboard and a pointing device (e.g., a mouse or a trackball) by which the user can provide input to the computer (e.g., interact with a user interface element). Other kinds of devices can be used to provide for interaction with a user. Other devices can be, for example, feedback provided to the user in any form of sensory feedback (e.g., visual feedback, auditory feedback, or tactile feedback). Input from the user can be, for example, received in any form, including acoustic, speech, and/or tactile input.

The computing device can include, for example, a computer, a computer with a browser device, a telephone, an IP phone, a mobile device (e.g., cellular phone, personal digital assistant (PDA) device, laptop computer, electronic mail device), and/or other communication devices. The computing device can be, for example, one or more computer servers. The computer servers can be, for example, part of a server farm. The browser device includes, for example, a computer (e.g., desktop computer, laptop computer, and tablet) with a World Wide Web browser (e.g., Microsoft® Internet Explorer® available from Microsoft Corporation, Chrome available from Google, Mozilla® Firefox available from Mozilla Corporation, Safari available from Apple). The mobile computing device includes, for example, a personal digital assistant (PDA).

Website and/or web pages can be provided, for example, through a network (e.g., Internet) using a web server. The web server can be, for example, a computer with a server module (e.g., Microsoft® Internet Information Services available from Microsoft Corporation, Apache Web Server available from Apache Software Foundation, Apache Tomcat Web Server available from Apache Software Foundation).

The storage module can be, for example, a random access memory (RAM) module, a read only memory (ROM) module, a computer hard drive, a memory card (e.g., universal serial bus (USB) flash drive, a secure digital (SD) flash card), a floppy disk, and/or any other data storage device. Information stored on a storage module can be maintained, for example, in a database (e.g., relational database system, flat database system) and/or any other logical information storage mechanism.

The above-described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

The above described networks can be implemented in a packet-based network, a circuit-based network, and/or a combination of a packet-based network and a circuit-based network. Packet-based networks can include, for example, the Internet, a carrier internet protocol (IP) network (e.g., local area network (LAN), wide area network (WAN), campus area network (CAN), metropolitan area network (MAN), home area network (HAN), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth®, code-division multiple access (CDMA) network, time division multiple access (TDMA) network, global system for mobile communications (GSM) network), and/or other circuit-based networks.

Some embodiments of the present invention may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that when executed cause a processor to execute method steps in accordance with embodiments. In some embodiments the instructions stores on the computer readable medium may be in the form of an installed application and in the form of an installation package.

Such instructions may be, for example, loaded by one or more processors and get executed. For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

In the foregoing detailed description, numerous specific details are set forth in order to provide an understanding of the invention. However, it will be understood by those skilled in the art that the invention can be practiced without these specific details. In other instances, well-known methods, procedures, and components, modules, units and/or circuits have not been described in detail so as not to obscure the invention. Some features or elements described with respect to one embodiment can be combined with features or elements described with respect to other embodiments.

The invention claimed is:

1. A computerized method for improving soft tissue analysis, the method comprising:
    obtaining, via a computing device, a plurality of radiological images of patient, where each of the radiological images is obtained using different excitations;
    selecting, by the computing device, a process among a plurality of processes to analyze the plurality of excitations based on an expected soft tissue type;
    segmenting, by the computer devices, the processed plurality of excitations to display the soft tissue;
    determining, via, the computing device, a first tissue type in a region of interest based on the plurality of radiological images of the patient, wherein the first tissue type is a represented by a grid of points across the region of interest; and
    determining, via the computing device, a second tissue type, in the region interest based on the plurality of radiological images of the patient, wherein the second tissue type is a focal region in the region of interest, wherein at least some of the grid points of the first tissue type coincide in position with the second tissue type.

2. The computerized method of claim 1 wherein the plurality of radiological image are computerized tomography (CT) images and the different excitations are different x-ray energy.

3. The computerized method of claim 1 wherein the plurality of radiological image are Magnetic Resonance (MR) images and the different excitations are different radio frequency pulses.

4. The computerized method of claim 1 wherein the plurality of radiological image are ultrasound images and the different excitations are different frequencies.

5. The computerized method of claim 1 wherein the plurality of processes comprises a digital subtraction process, digital addition process, a multivariate statistical process, or an excitation selection process.

6. The computerized method of claim 5 wherein the digital addition process comprises averaging the received plurality of radiological images.

7. The computerized method of claim 5 wherein the excitation selection process involves selecting a particular radiological image of the plurality of radiological images based on the tissue type.

8. The computerized method of claim 1 wherein the plurality of radiological images are CT images and each of the plurality of CT images are formed by:
directing, via a first x-ray source, a first x-ray attenuation to an energy integrating detector, wherein the energy integrated detector is dimensioned to produce an image of a predetermined area of the patient;
directing, via a second x-ray source, a second x-ray attenuation to a photon counting detector, where the photon counting detector to produce an image of a specific tissue target within the predetermined area; and
producing, via a processor, a final CT image based on the image of the predetermined area of the patient and the image of the specific tissue target within the predetermined image.

9. A computerized method for improving soft tissue analysis, the method comprising:
obtaining, via a computing device, a plurality of radiological images of patient, where each of the radiological images is obtained using different excitations;
selecting, by the computing device, a process among a plurality of processes to analyze the plurality of excitations based on an expected soft tissue type; and
segmenting, by the computer devices, the processed plurality of excitations to display the soft tissue,
wherein the plurality of processes comprises a digital subtraction process, digital addition process, a multivariate statistical process, or an excitation selection process, and wherein the digital subtraction process comprises subtracting a first subset of the plurality of radiological images from one or more of the plurality of radiological images not in the subset.

10. The computerized method of claim 9 wherein the plurality of radiological image are computerized tomography (CT) images and the different excitations are different x-ray energy.

11. The computerized method of claim 9 wherein the plurality of radiological image are Magnetic Resonance (MR) images and the different excitations are different radio frequency pulses.

12. A computerized method for improving soft tissue analysis, the method comprising:
obtaining, via a computing device, a plurality of radiological images of patient, where each of the radiological images is obtained using different excitations;
selecting, by the computing device, a process among a plurality of processes to analyze the plurality of excitations based on an expected soft tissue type; and
segmenting, by the computer devices, the processed plurality of excitations to display the soft tissue,
wherein the plurality of processes comprises a digital subtraction process, digital addition process, a multivariate statistical process, or an excitation selection process, and wherein the multivariate statistical process comprises:
combining the plurality of radiological images; and
removing inter-class dependencies through a multi-variate statistical approach.

13. The computerized method of claim 12 wherein the plurality of radiological image are computerized tomography (CT) images and the different excitations are different x-ray energy.

14. The computerized method of claim 12 wherein the plurality of radiological image are Magnetic Resonance (MR) images and the different excitations are different radio frequency pulses.

15. A computerized method for determining and displaying mixed tissue types, the method comprising:
receiving, via a computing device, a radiological image of a patient;
determining, via the computing device, a first tissue type in a region of interest based on the radiological image of the patient, wherein the first tissue type is represented by a grid of points across the region of interest; and
determining, via the computing device, a second tissue type, in the region of interest based on the radiological image of the patient, wherein the second tissue type is a focal region in the region of interest, wherein at least some of the grid points of the first tissue type coincide in position with the second tissue type.

16. The computerized method of claim 15 wherein the plurality of radiological image are computerized tomography (CT) images, Magnetic Resonance (MR) images, or ultrasound images.

17. The computerized method of claim 15 wherein the first tissue type and the second tissue type are overlaid when displayed.

18. The computerized method of claim 15 wherein the grid of points has varying densities.

19. The computerized method of claim 15 wherein the first tissue type is micro calcification, and the second tissue type is LNRC, dense calcification, or IPH.

20. The computerized method of claim 15 further comprising:
performing, via the computing device, multiple energy photon-counting K-edge subtraction imaging on the CT images;
performing, via the computing device, spectral image denoising with regularization models on the CT images;
improving the signal to noise ratio, via the computing device, of the calcium on the k-edge subtracted and de-noised CT images; and
segmenting, via the computing device, the improved calcium images to represent one or both of focally dense calcification and distributed microcalcification.

* * * * *